(12) United States Patent
Terasawa et al.

(10) Patent No.: US 10,435,421 B2
(45) Date of Patent: Oct. 8, 2019

(54) METHOD FOR PRODUCING N-SILYLAMINOALKYLSILANE COMPOUND

(71) Applicant: JNC CORPORATION, Tokyo (JP)

(72) Inventors: Junichi Terasawa, Kumamoto (JP);
Chisato Tsuruoka, Kumamoto (JP);
Toru Tanaka, Kumamoto (JP)

(73) Assignee: JNC CORPORATION, Tokyo (JP)

( * ) Notice: Subject to any disclaimer, the term of this patent is extended or adjusted under 35 U.S.C. 154(b) by 0 days.

(21) Appl. No.: 16/313,053

(22) PCT Filed: Jun. 6, 2017

(86) PCT No.: PCT/JP2017/020967
§ 371 (c)(1),
(2) Date: Dec. 24, 2018

(87) PCT Pub. No.: WO2018/003427
PCT Pub. Date: Jan. 4, 2018

(65) Prior Publication Data
US 2019/0225630 A1    Jul. 25, 2019

(30) Foreign Application Priority Data

Jul. 1, 2016 (JP) ................................ 2016-131246

(51) Int. Cl.
*C07F 7/18* (2006.01)
(52) U.S. Cl.
CPC ...................................... *C07F 7/18* (2013.01)
(58) Field of Classification Search
None
See application file for complete search history.

(56) References Cited

FOREIGN PATENT DOCUMENTS

| JP | H10-17579 | 1/1998 |
| JP | 2000327685 | 11/2000 |
| JP | 2009-249312 | 10/2009 |
| JP | 2009249312 A | * 10/2009 |

OTHER PUBLICATIONS

"International Search Report (Form PCT/ISA/210)" of PCT/JP2017/020967, dated Sep. 5, 2017, with English translation thereof, pp. 1-2.

* cited by examiner

*Primary Examiner* — Clinton A Brooks
*Assistant Examiner* — Kofi Adzamli
(74) *Attorney, Agent, or Firm* — JCIPRNET

(57) ABSTRACT

Shown is a method for producing an N-silylaminoalkylsilane compound. The N-silylaminoalkylsilane compound is produced by allowing an aminoalkylsilane compound to react with a monochlorosilane compound in the presence of a tertiary amine compound having an acid dissociation constant (pKa) of 7 or more and a polar surface area (PSA) of 12 Å² or more. The aminoalkylsilane compound is a compound represented by formula (1), for example. In formula (1), $R^1$ is alkyl having 1 to 5 carbons; $R^2$ is hydrogen, phenyl or 2-aminoethyl; m is 1, 2, 3, 4 or 5; and n is 0, 1 or 2. A reaction is as described in (ZZ) below, for example.

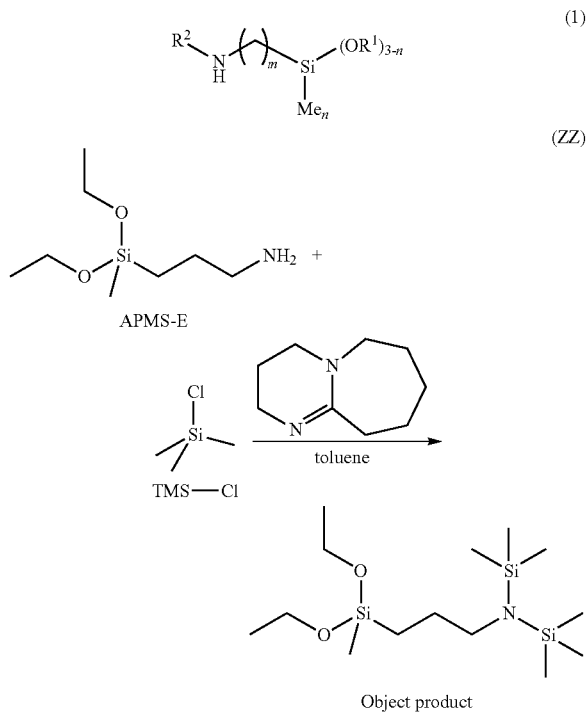

11 Claims, No Drawings

METHOD FOR PRODUCING N-SILYLAMINOALKYLSILANE COMPOUND

CROSS-REFERENCE TO RELATED APPLICATION

This application is a 371 application of the international PCT application serial no. PCT/JP2017/020967, filed on Jun. 6, 2017, which claims the priority benefit of Japan application no. 2016-131246, filed on Jul. 1, 2016. The entirety of each of the abovementioned patent applications is hereby incorporated by reference herein and made a part of this specification.

TECHNICAL FIELD

The invention relates to a method for producing an N-silylaminoalkylsilane compound.

BACKGROUND ART

In Patent Literature No. 1, N,N-bis(trimethylsilyl)aminopropylsilane is synthesized by a hydrosilylation reaction between N,N-bis(trimethylsilyl)allylamine and methyldialkoxysilane, but allylamine being a raw material of N,N-bis(trimethylsilyl)allylamine has high toxicity, and also requires use of an expensive platinum catalyst.

In Patent Literature No. 2, aminopropylsilane is allowed to react with trimethylchlorosilane in the presence of triethylamine, but in order to obtain an N-silylaminopropylsilane compound, a reaction has been required to be performed for a long period of time at room temperature. When both are heated in order to accelerate the reaction, a side reaction occurs to form a cyclic compound of trimethylsilane, and the like, and almost no N-silylaminopropylsilane compound is obtained.

Therefore, a desire has been expressed for a method for producing the N-silylaminoalkylsilane compound with high efficiency and in a short period of time.

CITATION LIST

Patent Literature

Patent literature No. 1: JP H10-17579 A.
Patent literature No. 2: JP 2009-249312 A.

SUMMARY OF INVENTION

Technical Problem

The invention provides a method for producing an N-silylaminoalkylsilane compound to be suitable for industrial production by dissolving problems of a conventional technology.

Solution to Problem

The present inventors have found that an N-silylaminoalkylsilane compound can be produced by allowing an aminoalkylsilane compound to react with a monochlorosilane compound by using a tertiary amine compound having a high acid dissociation constant (pKa) and a large polar surface area (PSA) as a dehydrochlorination agent, and have completed the invention.

Advantageous Effects of Invention

An advantage of the invention is capability of obtaining an N-silylaminoalkylsilane compound being an object product with a high yield.

DESCRIPTION OF EMBODIMENTS

The invention includes items described below. In addition, in chemical formulas, a symbol "Me" means methyl, and a symbol "Ph" means phenyl.

Item 1. A method for producing an N-silylaminoalkylsilane compound, wherein the N-silylaminoalkylsilane is produced by allowing an aminoalkylsilane compound to react with a monochlorosilane compound in the presence of a tertiary amine compound having an acid dissociation constant (pKa) of 7 or more and a polar surface area (PSA) of 12 Å$^2$ or more.

Item 2. The method for producing the N-silylaminoalkylsilane compound according to item 1, wherein the aminoalkylsilane compound is a compound represented by formula (1):

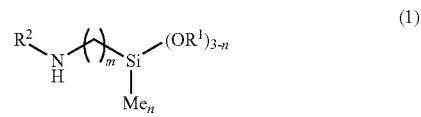

wherein, in formula (1),
R$^1$ is alkyl having 1 to 5 carbons; R$^2$ is hydrogen, phenyl or 2-aminoethyl; m is 1, 2, 3, 4 or 5; and n is 0, 1 or 2.

Item 3. The method for producing the N-silylaminoalkylsilane compound according to item 1 or 2, wherein the tertiary amine compound having the acid dissociation constant (pKa) of 7 or more and the polar surface area (PSA) of 12 Å$^2$ or more is an amine compound having at least one oxygen, or a conjugated amine compound having at least two nitrogens.

Item 4. The method for producing the N-silylaminoalkylsilane compound according to item 3, wherein the amine compound having at least one oxygen is 4-methylmorpholine.

Item 5. The method for producing the N-silylaminoalkylsilane compound according to item 3, wherein the conjugated amine compound having at least two nitrogens is a compound having an amidine skeleton.

Item 6. The method for producing the N-silylaminoalkylsilane compound according to item 5, wherein the compound having the amidine skeleton is a compound represented by formula (2):

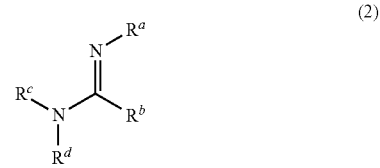

wherein, in formula (2),
R$^a$, R$^c$ and R$^d$ are independently alkyl having 1 to 5 carbons or alkenyl having 2 to 5 carbons; R$^b$ is hydrogen, alkyl having 1 to 5 carbons, alkenyl having 2 to 5 carbons, or amino in which two hydrogens are replaced by alkyl having 1 to 5 carbons; and two selected from $R^a$, $R^b$, $R^c$ and $R^d$ may be bonded with each other to form a ring.

Item 7. The method for producing the N-silylaminoalkylsilane compound according to item 5 or 6, wherein the compound having the amidine skeleton is a heterocyclic compound.

Item 8. The method for producing the N-silylaminoalkylsilane compound according to item 5 or 6, wherein the compound having the amidine skeleton is 1,8-diazabicyclo[5.4.0]undec-7-ene.

Item 9. The method for producing the N-silylaminoalkylsilane compound according to any one of items 1 to 8, wherein a compound represented by formula (3), (4) or (5) is taken as an object product:

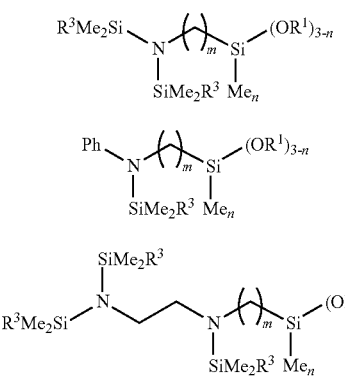

wherein, in formulas (3), (4) and (5), $R^1$ is alkyl having 1 to 5 carbons; $R^3$ is hydrogen, alkyl having 1 to 5 carbons or phenyl; m is 1, 2, 3, 4 or 5; and n is 0, 1 or 2.

The aminoalkylsilane compound that is a raw material according to the invention is preferably the compound represented by formula (1).

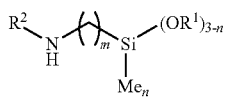

In formula (1), $R^1$ is alkyl having 1 to 5 carbons; $R^2$ is hydrogen, phenyl or 2-aminoethyl; m is 1, 2, 3, 4 or 5; and n is 0, 1 or 2.

Specific examples of the compound represented by formula (1) include 3-aminopropylmethyldiethoxysilane, 3-aminopropyltriethoxysilane, 3-aminopropylmethyldimethoxysilane, 3-aminopropyltrimethoxysilane, 3-anilinopropylmethyldiethoxysilane, 3-anilinopropyltriethoxysilane, 3-anilinopropylmethyldimethoxysilane, 3-anilinopropyltrimethoxysilane, N-(2-aminoethyl)-3-aminopropylmethyldimethoxysilane, N-(2-aminoethyl)-3-aminopropyltrimethoxysilane, 1-aminomethylmethyldiethoxysilane, 1-aminomethyltriethoxysilane, 2-aminoethylmethyldiethoxysilane and 2-aminoethyltriethoxysilane.

The monochlorosilane compound is used as the other raw material. Preferred monochlorosilane compound is a compound represented by formula (6).

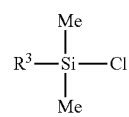

In formula (6), $R^3$ is hydrogen, alkyl having 1 to 5 carbons or phenyl.

Specific examples of the monochlorosilane compound include trimethylchlorosilane, dimethylchlorosilane, ethyldimethylchlorosilane, vinyldimethylchlorosilane and phenyldimethylchlorosilane.

An amount of the monochlorosilane compound to be added thereto in the reaction is preferably an equal-fold mole or greater based on hydrogen in amine in the aminopropylsilane compound. The amount thereof is more preferably in the range from 1-fold mole to 3-fold moles, and further preferably in the range from 1-fold mole to 2-fold moles.

In the tertiary amine compound to be used according to the invention, the acid dissociation constant (pKa) is 7 or more, and the polar surface area (PSA) is 12 Å$^2$ or more.

The acid dissociation constant (pKa) and the polar surface area (PSA) can be calculated by Advanced Chemistry Development (ACD/Labs) Software V11.02 (c1994-2016 ACD/Labs), respectively. For example, each value thereof can be obtained from database SciFinder (registered trademark).

The tertiary amine compound to be used according to the invention is used as the dehydrochlorination agent, and therefore is required to be a base, and is preferably required to be a stronger base. Accordingly, the acid dissociation constant (pKa) is required to be 7 or more, and the polar surface area (PSA) is required to be 12 Å$^2$ or more. Then, in order to avoid a substitution reaction of a strong base amine compound, hydrogen directly bonded to nitrogen in the amine is preferably absent, and therefore the tertiary amine is selected.

The tertiary amine compound having the acid dissociation constant (pKa) of 7 or more and the polar surface area (PSA) of 12 Å$^2$ or more is preferably an amine compound having at least one oxygen, or a conjugated amine compound having at least two nitrogens.

The amine compound having at least one oxygen is preferably 4-methylmorpholine.

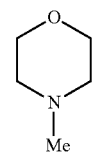

4-metylmorpholine

Specific examples of the conjugated amine compound having at least two nitrogens include a heterocyclic compound and N,N-dimethyl-4-aminopyridine (DMAP).

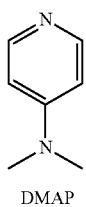

DMAP

The conjugated amine compound having at least two nitrogens, which is used as the dehydrochlorination agent, is preferably a compound having the amidine skeleton. The compound having the amidine skeleton is preferably the compound represented by formula (2).

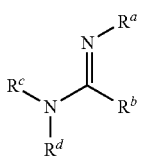

(2)

In formula (2), $R^a$, $R^c$ and $R^d$ are independently alkyl having 1 to 5 carbons or alkenyl having 2 to 5 carbons; $R^b$ is hydrogen, alkyl having 1 to 5 carbons, alkenyl having 2 to 5 carbons or amino in which two hydrogens are replaced by alkyl having 1 to 5 carbons; and two selected from $R^a$, $R^b$, $R^c$ and $R^d$ may be bonded with each other to form a ring.

Specific examples of the compound represented by formula (2) include compounds described below.

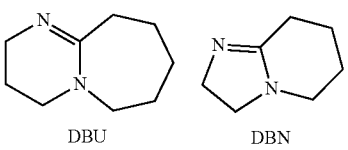

DBU          DBN

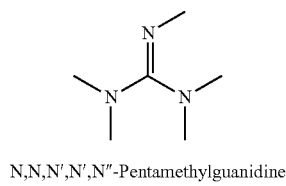

N,N,N',N',N''-Pentamethylguanidine

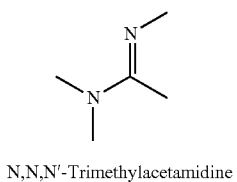

N,N,N'-Trimethylacetamidine

The dehydrochlorination agent further preferably used is the heterocyclic compound. Specific examples of the heterocyclic compound include 1,8-diazabicyclo[5.4.0]undec-7-ene (DBU: registered trademark) and 1,5-diazabicyclo[4.3.0]non-5-ene (DBN).

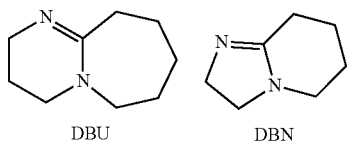

DBU          DBN

The most preferred dehydrochlorination agent is DBU.

An amount of the amine compound having the acid dissociation constant (pKa) of 7 or more and the polar surface area (PSA) of 12 Å² or more, which is added thereto in the reaction, is preferably an equal-fold mole or greater based on the hydrogen in the amine in the aminopropylsilane compound. The amount thereof is more preferably in the range from 1-fold mole to 3-fold moles, and further preferably in the range from 1-fold mole to 2-fold moles.

In the reaction according to the invention, a solvent is preferably used. As the solvent, a hydrocarbon-based nonpolar solvent such as benzene, toluene, n-hexane and n-heptane is preferred. An amount of the solvent to be used is preferably adjusted to an amount in which a slurry concentration of hydrochloride of the amine formed in a reaction system becomes less than 40%.

In the production method according to the invention, the reaction progresses by charging the aminoalkylsilane compound, the monochlorosilane compound and the tertiary amine compound having the acid dissociation constant (pKa) of 7 or more and the polar surface area (PSA) of 12 Å² or more, and mixing the resulting mixture. In order to allow the reaction to progress while preferably controlling the reaction, the monochlorosilane compound and the tertiary amine compound are preferably dissolved in the solvent, and then a temperature of the resulting mixture is adjusted to a predetermined reaction temperature, and then the aminoalkylsilane compound is preferably added dropwise thereto.

The reaction temperature is preferably in the range from 0° C. to 100° C., further preferably in the range from 10° C. to 80° C., and still further preferably in the range from 20° C. to 60° C. The reaction is promoted at a higher temperature, and then the resulting mixture can also be aged at a low temperature.

A pressure of the reaction is not particularly limited, but if an atmosphere is decompressed, the monochlorosilane compound having a low boiling point is easily volatilized, and therefore the pressure is preferably a normal pressure or higher.

The reaction is preferably performed under flow of dry air or dry nitrogen for the purpose of preventing mixing of moisture. A flammable material is handled in the reaction, and therefore an environment under an inert atmosphere such as nitrogen or argon is preferred, for example.

When the compounds represented by formulas (3), (4) and (5) are taken as the object products, the reaction according to the invention can be preferably used.

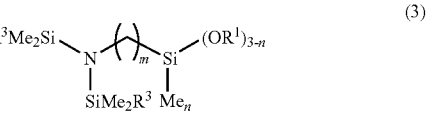

(3)

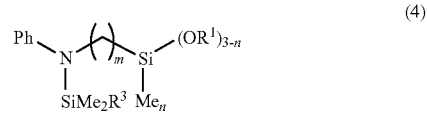

(4)

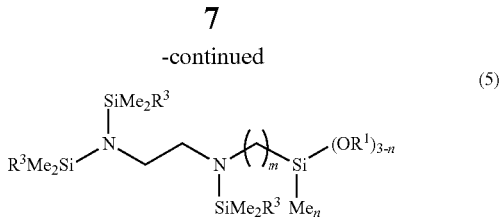

In formulas (3), (4) and (5), $R^1$ is alkyl having 1 to 5 carbons; $R^3$ is hydrogen, alkyl having 1 to 5 carbons or phenyl; m is 1, 2, 3, 4 or 5; and n is 0, 1 or 2.

In the compound represented by formula (1), when $R^2$ is hydrogen, the compound represented by formula (3) serves as the object product. When $R^2$ is phenyl, the compound represented by formula (4) serves as the object product. When $R^2$ is 2-aminoethyl, the compound represented by formula (5) serves as the object product.

EXAMPLES

Next, the invention will be described in greater detail by way of Examples. The invention is not limited by the Examples.

Compounds were prepared by the procedures described below. The prepared compounds were identified by NMR analysis, and quantitatively determined by gas chromatographic analysis.

NMR analysis: For measurement, ECP400 made by JEOL Ltd. was used. In $^1$H-NMR measurement, a sample was dissolved in a deuterated solvent such as CDCl$_3$, and measurement was carried out under conditions of room temperature, 400 MHz and 32 times of accumulation. Chloroform was used as an internal standard. In $^{13}$C-NMR measurement, CDCl$_3$ was used as an internal standard, and measurement was carried out under conditions of 512 times of accumulation. In explaining nuclear magnetic resonance spectra obtained, s, d, t, q, quin and m stand for a singlet, a doublet, a triplet, a quartet, a quintet and a multiplet, respectively.

For example, spectrum data of N,N-bis(trimethylsilyl)-3-aminopropylmethyldiethoxysilane that is one of object products will be shown.

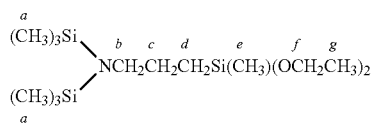

| | Chemical shift: δ (ppm) | |
|---|---|---|
| | $^1$H-NMR | $^{13}$C-NMR |
| a | 0.07 (18H, s) | 2.04 |
| b | 2.68-2.73 (2H, m) | 48.8 |
| c | 1.35-1.38 (2H, m) | 28.4 |
| d | 0.44-0.49 (2H, m) | 11.1 |
| e | 0.1 (3H, s) | -4.89 |
| f | 3.75 (4H, q) | 58.0 |
| g | 1.21 (6H, t) | 18.4 |

Gas chromatographic analysis: For measurement, GC-2014 Gas Chromatograph made by Shimadzu Corporation was used. As a column, a packed column: a bore of 2.6 mm and a length of 3 m, and a packing material: SE-30, 10%, 60/80, Shimalite WAW were used. As a carrier gas, helium (20 mL/minute) was used. A temperature of a sample vaporization chamber and a temperature of a detector (TCD) part were set to 250° C. and 250° C., respectively. A sample was filtrated by a 0.5 μm syringe filter, and then 1 μL of filtrate was injected into the sample vaporization chamber. As a recorder, GC Solution System made by Shimadzu Corporation or the like was used.

Example 1

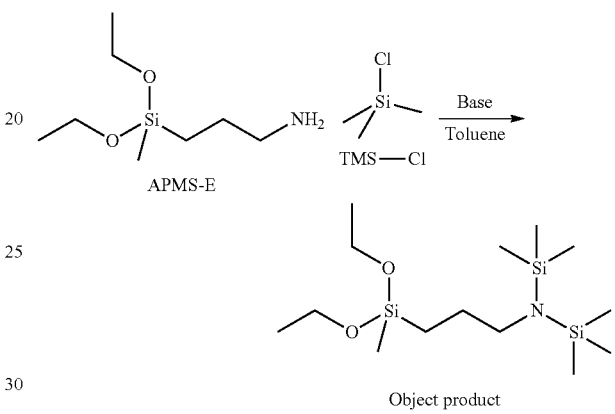

A system inside a 100 mL four-necked flask was replaced by nitrogen, and then 17.4 g of toluene, 10.4 g (69 mmol) of DBU and 7.3 g (67 mmol) of trimethylchlorosilane were put therein under room temperature. The resulting mixture was heated to 50° C. while stirring the resulting mixture, and 5.0 g (26.5 mmol) of 3-aminopropylmethyldiethoxysilane (APMS-E) was added thereto. Then, the resulting mixture was stirred at 50° C. for 1 hour, and further heated to 60° C. and stirred for 3 hours. Then, the resulting mixture was cooled to room temperature, and aged for about 20 hours. A gas chromatographic analysis was conducted, and N,N-bis(trimethylsilyl)-3-aminopropylmethyldiethoxysilane being an object product was obtained with a GC yield of 93.9%.

The following compounds, including DBU used in Example 1, are taken as base 1 to base 12.

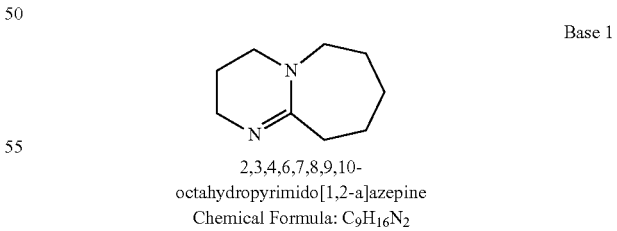

Base 1

2,3,4,6,7,8,9,10-octahydropyrimido[1,2-a]azepine
Chemical Formula: $C_9H_{16}N_2$

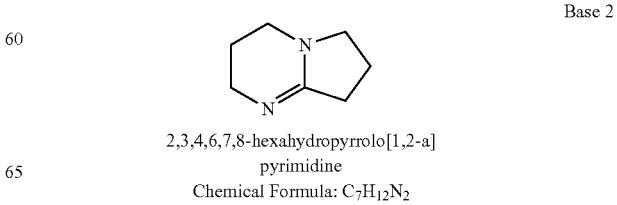

Base 2

2,3,4,6,7,8-hexahydropyrrolo[1,2-a]pyrimidine
Chemical Formula: $C_7H_{12}N_2$

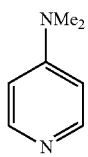

DMAP
Chemical Formula: $C_7H_{10}N_2$

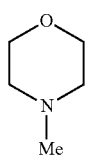

4-methylmorpholine
Chemical Formula: $C_5H_{11}NO$

Pyridine
Chemical Formula: $C_5H_5N$

1-Methypyrrole
Chemical Formula: $C_5H_7N$

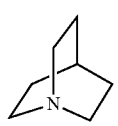

Quinuclidine
Chemical Formula: $C_7H_{13}N$

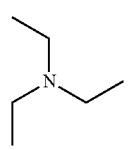

TEA
Chemical Formula: $C_6H_{15}N$

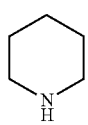

Piperidine
Chemical Formula: $C_5H_{11}N$

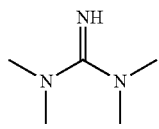

1,1,3,3-Tetramethyl guanidine
Chemical Formula: $C_5H_{13}N_3$

Base 3
Base 4
Base 5
Base 6
Base 7
Base 8
Base 9
Base 10
Base 11

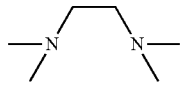

TMEDA
Chemical Formula: $C_6H_{16}N_2$

Base 12

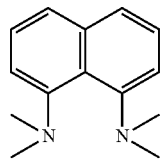

ProtonSponge
Chemical Formula: $C_{14}H_{18}N_2$

Values of acid dissociation constants (pKa) and polar surface areas (PSA) of bases 1 to 12 were obtained from database SciFinder (registered trademark).

| | | | Chemical structure | Physical properties | |
|---|---|---|---|---|---|
| | | Base | Tertiary amine | pKa | PSA (Å²) |
| Example 1 | Base 1 | DBU | Yes | 13.28 | 15.60 |
| Example 2 | Base 2 | DBN | Yes | 13.42 | 15.60 |
| Example 3 | Base 3 | DMAP | Yes | 9.52 | 16.10 |
| Example 4 | Base 4 | 4-Methymorpholine | Yes | 7.58 | 12.50 |
| Comparative Example 1 | Base 5 | Pyridine | Yes | 5.23 | 12.90 |
| Comparative Example 2 | Base 6 | 1-Methlpyrrole | Yes | -2.80 | 4.93 |
| Comparative Example 3 | Base 7 | Quinuclidine | Yes | 10.87 | 3.24 |
| Comparative Example 4 | Base 8 | TEA | Yes | 10.62 | 3.24 |
| Comparative Example 5 | Base 9 | Piperidine | No | 10.45 | 12.00 |
| Comparative Example 6 | Base 10 | 1,1,3,3-tetrametylguanidine | No | 15.20 | 30.30 |
| Comparative Example 7 | Base 11 | TMEDA | Yes | 8.86 | 6.48 |
| Comparative Example 8 | Base 12 | Protone-Sponge | Yes | 12.40 | 6.48 |

Examples 2 to 4

A formation reaction was performed by applying the same mole ratio of raw materials or the like, the same reaction apparatus and the same reaction method each as in Example 1 by using bases 2 to 4 each in place of DBU (base 1) used in Example 1, and adjusting aminosilane, chlorosilane and toluene in use therefor to be the same as in Example 1.

Comparative Examples 1 to 8

A formation reaction was performed by applying the same mole ratio of raw materials or the like, the same reaction apparatus and the same reaction method each as in Example 1 by using bases 5 to 12 each in place of DBU (base 1) used in Example 1, and adjusting aminosilane, chlorosilane and toluene in use therefor to be the same as in Example 1.

A cyclized product of (1-trimethylsilyl-2,2-diethoxy-1-aza-2-silacyclopentane) and a mono-substituted product of (N-trimethylsilyl-3-aminopropylmethyldiethoxysilane) were obtained as by-products depending on the reaction.

Compositions after the reaction in Examples 1 to 4 and Comparative Examples 1 to 8 are shown. As the composition, a proportion of each component was expressed by a percentage based on a total of GC % of the aminosilane being the raw material, the object product, the cyclized product and the mono-substituted product.

In Comparative Examples 1 to 8, a large amount of unreacted aminosilane remained, and the cyclized product and the mono-substituted product were by-produced. On the other hand, in Examples 1 to 4, N,N-bis(trimethylsilyl)-3-aminopropylmethyldiethoxysilane being the object product was able to be obtained with a satisfactory yield.

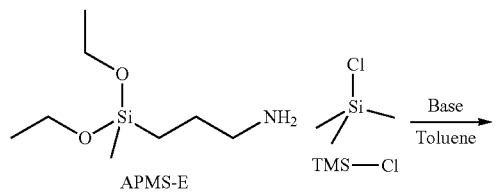

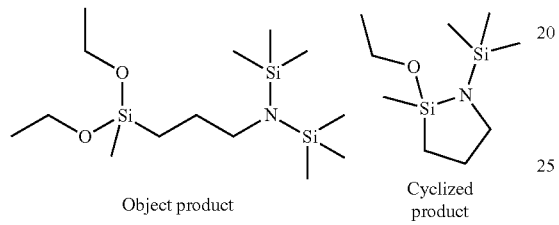

Example 5

A formation reaction was performed by applying the same mole ratio of raw materials or the like, the same reaction apparatus and the same reaction method each as in Example 1 by using phenyldimethylchlorosilane in place of trimethylchlorosilane used in Example 1, and adjusting aminoalkylsilane, a base and toluene in use therefor to be the same as in Example 1.

Comparative Example 9

A formation reaction was performed by applying the same mole ratio of raw materials or the like, the same reaction apparatus and the same reaction method each as in Example 1 by using phenyldimethyl phenyldimethylchlorosilane silane in place of trimethylchlorosilane and TEA (base 8) in place of DBU (base 1) used in Example 1, and adjusting aminoalkylsilane and toluene in use therefor to be the same as in Example 1.

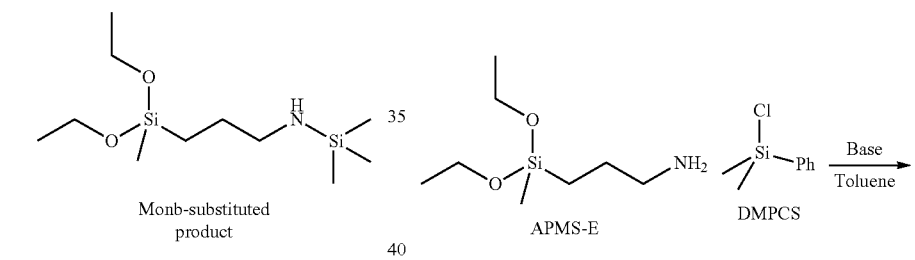

|  | Base |  | Compositions after reaction (%) | | | |
|---|---|---|---|---|---|---|
|  |  |  | APMS-E | Object product | Cyclized product | Mono-substituted product |
| Example 1 | Base 1 | DBU | 6.1 | 93.9 | 0.0 | 0.0 |
| Example 2 | Base 2 | DBN | 3.6 | 96.4 | 0.0 | 0.0 |
| Example 3 | Base 3 | DMAP | 9.9 | 82.8 | 0.5 | 6.8 |
| Example 4 | Base 4 | 4-Methymorpholine | 30.2 | 65.8 | 4.0 | 0.0 |
| Comparative Example 1 | Base 5 | Pyridine | 72.8 | 0.0 | 27.2 | 0.0 |
| Comparative Example 2 | Base 6 | 1-Methlpyrrole | 47.1 | 0.0 | 52.9 | 0.0 |
| Comparative Example 3 | Base 7 | Quinuclidine | 85.6 | 7.4 | 0.0 | 7.0 |
| Comparative Example 4 | Base 8 | TEA | 63.3 | 3.2 | 33.5 | 0.0 |
| Comparative Example 5 | Base 9 | Piperidine | 6.6 | 3.9 | 0.0 | 89.6 |
| Comparative Example 6 | Base 10 | 1,1,3,3-tetrametylguanidine | 85.2 | 11.3 | 3.6 | 0.0 |
| Comparative Example 7 | Base 11 | TMEDA | 77.3 | 2.0 | 20.7 | 0.0 |
| Comparative Example 8 | Base 12 | Protone-Sponge | 52.5 | 0.0 | 47.5 | 0.0 |

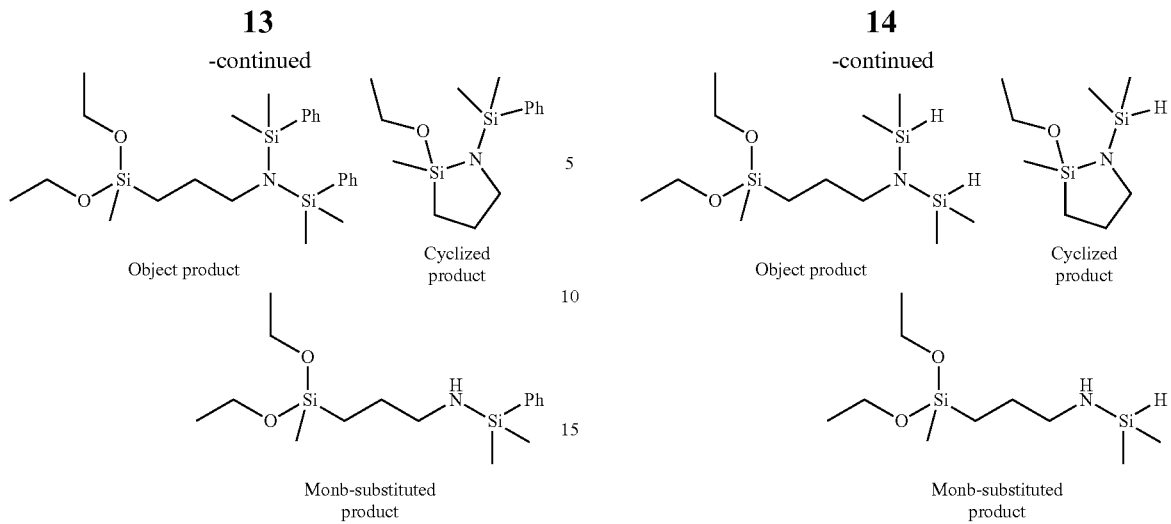

|  | | Base | APMS-E | Compositions after reaction (%) | | |
|---|---|---|---|---|---|---|
|  | | | | Object product | Cyclized product | Mono-substituted product |
| Example 5 | Base 1 | DBU | 7.4 | 73.7 | 0.0 | 18.9 |
| Comparative Example 9 | Base 8 | TEA | 22.2 | 0.0 | 0.0 | 77.8 |

|  | | Base | APMS-E | Compositions after reaction (%) | | |
|---|---|---|---|---|---|---|
|  | | | | Object product | Cyclized product | Mono-substituted product |
| Example 6 | Base 1 | DBU | 43.7 | 44.5 | 0.0 | 11.8 |
| Comparative Example 10 | Base 8 | TEA | 13.5 | 0.0 | 1.5 | 85.0 |

In Comparative Example 9, a large amount of unreacted aminoalkylsilane remained, and a large amount of a mono-substituted product was by-produced. On the other hand, in Example 5, N,N-bis(phenyldimethylsilyl)-3-aminopropylmethyldiethoxysilane being an object product was able to be obtained with a satisfactory yield.

Example 6

A formation reaction was performed by applying the same mole ratio of raw materials or the like, the same reaction apparatus and the same reaction method each as in Example 1 by using dimethylchlorosilane in place of trimethylchlorosilane used in Example 1, and adjusting aminoalkylsilane, a base and toluene in use therefor to be the same as in Example 1.

Comparative Example 10

A formation reaction was performed by applying the same mole ratio of raw materials or the like, the same reaction apparatus and the same reaction method each as in Example 1 by using dimethylchlorosilane in place of trimethylchlorosilane and TEA (base 8) in place of DBU (base 1) used in Example 1, and adjusting aminoalkylsilane and toluene in use therefor to be the same as in Example 1.

In Comparative Example 10, most of a product was a mono-substituted product and almost no object product was obtained. On the other hand, in Example 6, a larger amount of an object product was obtained.

Example 7

A formation reaction was performed by applying the same mole ratio of raw materials or the like, the same reaction apparatus and the same reaction method each as in Example 1 by using vinyldimethylchlorosilane in place of trimethylchlorosilane used in Example 1, and adjusting aminoalkylsilane, a base and toluene in use therefor to be the same as in Example 1.

Comparative Example 11

A formation reaction was performed by applying the same mole ratio of raw materials or the like, the same reaction apparatus and the same reaction method each as in Example 1 by using vinyldimethylchlorosilane in place of trimethylchlorosilane and TEA (base 8) in place of DBU (base 1) used in Example 1, and adjusting aminoalkylsilane and toluene in use therefor to be the same as in Example 1.

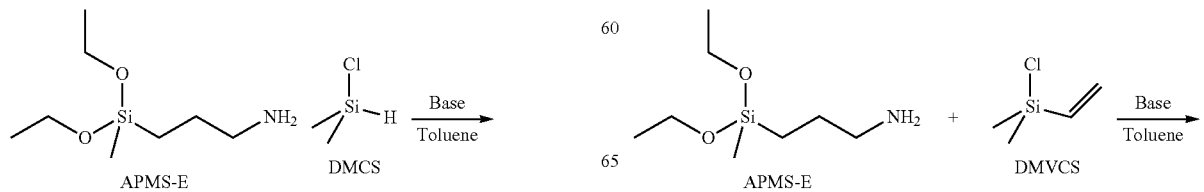

-continued

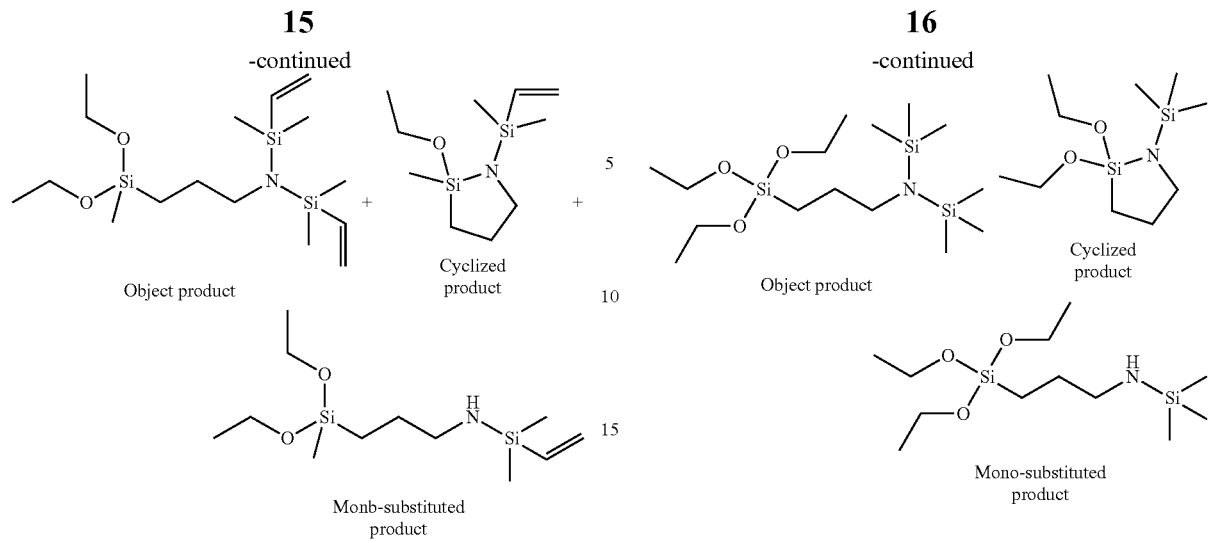

| | Base | APMS-E | Compositions after reaction (%) | | |
|---|---|---|---|---|---|
| | | | Object product | Cyclized product | Mono-substituted product |
| Example 7 | Base 1 | DBU | 5.8 | 94.2 | 0.0 | 0.0 |
| Comparative Example 11 | Base 8 | TEA | 8.3 | 0.0 | 1.2 | 88.5 |

In Comparative Example 11, most of a product was a mono-substituted product and almost no object product was obtained. On the other hand, in Example 6, a larger amount of an object product was obtained.

Example 8

A formation reaction was performed by applying the same mole ratio of raw materials or the like, the same reaction apparatus and the same reaction method each as in Example 1 by using 3-aminopropyltriethoxysilane (S330) in place of 3-aminopropylmethyldiethoxysilane (APMS-E) used in Example 1, and adjusting monochlorosilane, a base and toluene in use therefor to be the same as in Example 1.

Comparative Example 12

A formation reaction was performed by applying the same mole ratio of raw materials or the like, the same reaction apparatus and the same reaction method each as in Example 1 by using 3-aminopropyltriethoxysilane (S330) in place of 3-aminopropylmethyldiethoxysilane (APMS-E) and TEA (base 8) in place of DBU (base 1) used in Example 1, and adjusting monochlorosilane and toluene in use therefor to be the same as in Example 1.

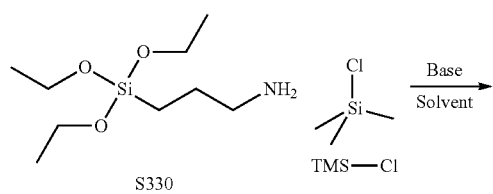

| | Base | APMS-E | Compositions after reaction (%) | | |
|---|---|---|---|---|---|
| | | | Object product | Cyclized product | Mono-substituted product |
| Example 8 | Base 1 | DBU | 5.0 | 88.2 | 0.0 | 6.7 |
| Comparative Example 12 | Base 8 | TEA | 3.6 | 0.0 | 99.6 | 0.0 |

Example 9

A formation reaction was performed by applying the same reaction apparatus and the same reaction method each as in Example 1 by using 3-(N-phenylamino)propylmethyltrimethoxysilane in place of 3-aminopropylmethyldiethoxysilane used in Example 1, and adjusting toluene to 20.0 g, trimethylchlorosilane to 2.44 g (22.50 mmol), DBU (base 1) to 3.87 g (25.43 mmol) and 3-(N-phenylamino)propylmethyltrimethoxysilane to 5.0 g (19.56 mmol).

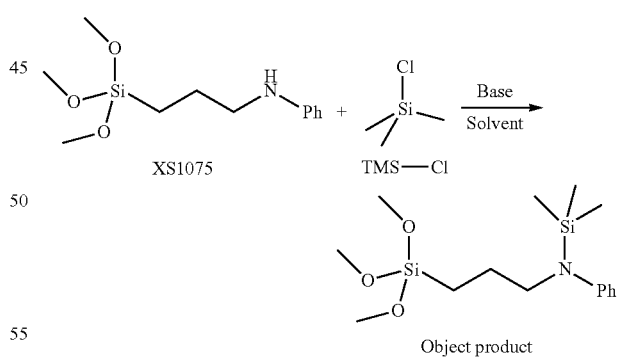

As a composition of the reaction liquid, 97.94% of 3-(N-phenyl-N-trimethylsilylamino)propylmethyltrimethoxysilane being an object product was obtained with 2.06% of aminosilane being a raw material, and the object product was obtained with a high yield.

INDUSTRIAL APPLICABILITY

An N-silylaminoalkylsilane compound that can be produced according to the invention is a useful compound as a raw material for producing aminoalkyl-modified silicone, or a raw material of a silane coupling agent, a surface treatment agent and various silane coupling agents for a fuel efficient tire or the like.

What is claimed is:

1. A method for producing an N-silylaminoalkylsilane compound, wherein the N-silylaminoalkylsilane is produced by allowing an aminoalkylsilane compound to react with a monochlorosilane compound in the presence of a tertiary amine compound having an acid dissociation constant of 7 or more and a polar surface area of 12 Å² or more.

2. The method for producing the N-silylaminoalkylsilane compound according to claim 1, wherein the aminoalkylsilane compound is a compound represented by formula (1):

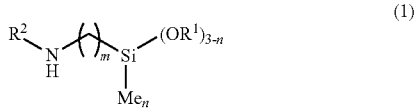

(1)

wherein, in formula (1),
$R^1$ is alkyl having 1 to 5 carbons; $R^2$ is hydrogen, phenyl or 2-aminoethyl; m is 1, 2, 3, 4 or 5; and n is 0, 1 or 2.

3. The method for producing the N-silylaminoalkylsilane compound according to claim 1, wherein the tertiary amine compound having the acid dissociation constant of 7 or more and the polar surface area of 12 Å² or more is an amine compound having at least one oxygen, or a conjugated amine compound having at least two nitrogens.

4. The method for producing the N-silylaminoalkylsilane compound according to claim 3, wherein the amine compound having at least one oxygen is 4-methylmorpholine.

5. The method for producing the N-silylaminoalkylsilane compound according to claim 3, wherein the conjugated amine compound having at least two nitrogens is a compound having an amidine skeleton.

6. The method for producing the N-silylaminoalkylsilane compound according to claim 5, wherein the compound having the amidine skeleton is a compound represented by formula (2):

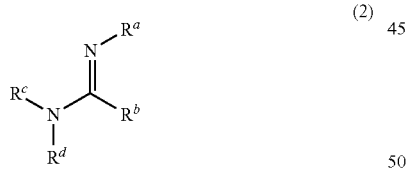

(2)

wherein, in formula (2),
$R^a$, $R^c$ and $R^d$ are independently alkyl having 1 to 5 carbons or alkenyl having 2 to 5 carbons; $R^b$ is hydrogen, alkyl having 1 to 5 carbons, alkenyl having 2 to 5 carbons, or amino in which two hydrogens are replaced by alkyl having 1 to 5 carbons; and
two selected from $R^a$, $R^b$, $R^c$ and $R^d$ may be bonded with each other to form a ring.

7. The method for producing the N-silylaminoalkylsilane compound according to claim 6, wherein the compound having the amidine skeleton is a heterocyclic compound.

8. The method for producing the N-silylaminoalkylsilane compound according to claim 6, wherein the compound having the amidine skeleton is 1,8-diazabicyclo[5.4.0]undec-7-ene.

9. The method for producing the N-silylaminoalkylsilane compound according to claim 5, wherein the compound having the amidine skeleton is a heterocyclic compound.

10. The method for producing the N-silylaminoalkylsilane compound according to claim 5, wherein the compound having the amidine skeleton is 1,8-diazabicyclo[5.4.0]undec-7-ene.

11. The method for producing the N-silylaminoalkylsilane compound according to claim 1, wherein the compound represented by formula (3), (4) or (5) is taken as an object product:

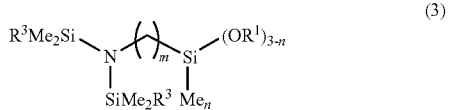

(3)

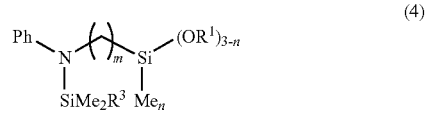

(4)

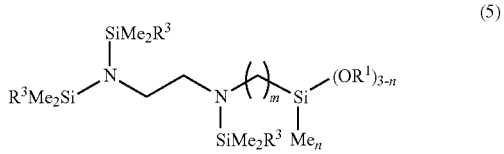

(5)

wherein, in formulas (3), (4) and (5),
$R^1$ is alkyl having 1 to 5 carbons; $R^3$ is hydrogen, alkyl having 1 to 5 carbons or phenyl; m is 1, 2, 3, 4 or 5; and n is 0, 1 or 2.

* * * * *